United States Patent
Dangelmayer et al.

[11] Patent Number: 6,016,246
[45] Date of Patent: Jan. 18, 2000

[54] WRIST STRAP

[75] Inventors: George Theodore Dangelmayer, Plaistow, N.H.; Louis F. DeChiaro, Lanoka Harbor, N.J.; John Philip Franey, Bridgewater, N.J.; Min-Chung Jon, Princeton Junction, N.J.

[73] Assignee: Lucent Technologies Inc., Murray Hill, N.J.

[21] Appl. No.: 09/211,180

[22] Filed: Dec. 14, 1998

[51] Int. Cl.[7] .................................................. H05F 3/02
[52] U.S. Cl. ......................................... 361/220; 361/212
[58] Field of Search ........................... 361/212, 220–224; 239/152, 153; 63/1.11, 1.12, 1.14; 439/5, 178, 179

[56] References Cited

U.S. PATENT DOCUMENTS

| | | | |
|---|---|---|---|
| 2,235,350 | 3/1941 | Anderson . | |
| 3,977,392 | 8/1976 | Manley | 128/2.1 E |
| 4,265,253 | 5/1981 | Abraham | 128/798 |
| 4,751,548 | 6/1988 | Lawson | 361/212 |
| 4,762,497 | 8/1988 | Burvee | 439/179 |
| 4,810,418 | 3/1989 | Burvee | 361/212 |

*Primary Examiner*—Fritz Fleming

[57] ABSTRACT

The present invention in some embodiments provides for an apparatus comprised of a conductive strap and a lotion dispensing device connected to the conductive strap. The lotion dispensing device is comprised of a lotion storage device such as a reservoir, a permeable membrane, or a sponge. Preferably a person would put on the conductive strap and the lotion dispensing device in order to eliminate or reduce the transmission of static discharge to electronic circuitry and to minimize static discharge events that could interrupt the operation of electronic systems. The conductive strap includes a plurality of holes and the plurality of holes. The permeable membrane may be of a material, which dispenses lotion from the permeable membrane at a rate which is increased with heat. The size of holes in the conductive strap may increase in response to greater heat levels. The lotion dispensing device may be comprised of a reservoir filled with lotion. A grounding wire is preferably connected from the conductive strap to ground and preferably incorporates a resistance of about 1 mega-ohms. The conductive strap is preferably in the form of an elastic wrist band or watch band.

20 Claims, 5 Drawing Sheets

WRIST STRAP

FIELD OF THE INVENTION

This invention relates to improved methods and apparatus for preventing electronic circuits from being impacted by static discharge.

BACKGROUND OF THE INVENTION

Electronic circuits, particularly in the last fifteen years, have become highly susceptible to static charge generation. Electronic systems have also become more susceptible to interruption of normal service caused by static discharge events in the near vicinity. Static charges, such as those found on people, can very easily destroy the effectiveness of electronic circuits. This can occur by, for example, a person shuffling his feet on the floor and then touching an electronic circuit. The same charges can easily interrupt the proper operation of many advanced types of electronic systems. This can occur by a person shuffling his/her feet on the floor and then touching any metallic objects in the near vicinity of an operating system.

One approach to eliminating static discharge, is to have a person wear a wrist strap comprised of a conductive strap, which is connected to a grounding wire. The grounding wire typically has a 1 mega-ohm resistance incorporated with it or in series with it. Thus the static charges on the person or the person's clothing would dissipate through the conductive strap and into the grounding wire. However, in order for this technique to work the person's skin itself must be conductive. The skin is conductive if natural fluids are present, but if the skin dries out then it is not conductive. In order to make the skin conductive after it has dried out, lotions have been applied to a person's hands and wrists. However, because the individual never knows when to apply the lotion, lack of conductivity may occur, and static discharges from contact with a person or with a person's clothing may destroy circuitry or interrupt the operation of electronic systems.

In some instances a person's skin may be dry in one area and conductive in another, allowing static charges to be communicated to circuitry but not allowing charges to dissipate through wrist straps known in the art.

SUMMARY OF THE INVENTION

The present invention in some embodiments provides for an apparatus comprised of a conductive strap and a lotion dispensing device connected to or incorporated in the conductive strap. Preferably a person would put on the conductive strap and the lotion dispensing device in order to eliminate or reduce the transmission of static discharge to electronic circuitry.

The conductive strap preferably includes a plurality of holes and the plurality of holes of the conductive strap are preferably part of the lotion dispensing device. The lotion dispensing device can be comprised of a lotion storage device such as a permeable membrane, a reservoir, a sponge, or some other lotion storage device. Generally speaking lotion contained with a lotion storage device, preferably flows out through holes in the conductive strap and onto an individual's skin.

The permeable membrane may be of a type of material, such as microperforated polyethylene ("PE") or polypropylene ("PP"), which dispenses lotion from the permeable membrane at a rate which is increased with heat, which is preferably body heat. The reservoir may be bounded by layers to prevent lotion from flowing out of the reservoir. The size of holes in the conductive strap may increase in response to greater heat levels which may preferably be greater body heat levels. A grounding wire is preferably connected from the conductive strap to ground which is typically on the wrist of an individual. The conductive strap is preferably a conductive wrist strap band. The grounding wire preferably incorporates a resistance of about 1 mega-ohm (1 million ohms).

The conductive strap is preferably in the form of an elastic wrist band or metallic watch band.

The conductive strap broadly includes straps that are designed to reduce electromagnetic interference ("EMI") events as well as the component damaging Electro static discharge ("ESD") events.

BRIEF DESCRIPTIONS OF THE DRAWINGS

DETAILED DESCRIPTION OF THE DRAWINGS

Figure 1:
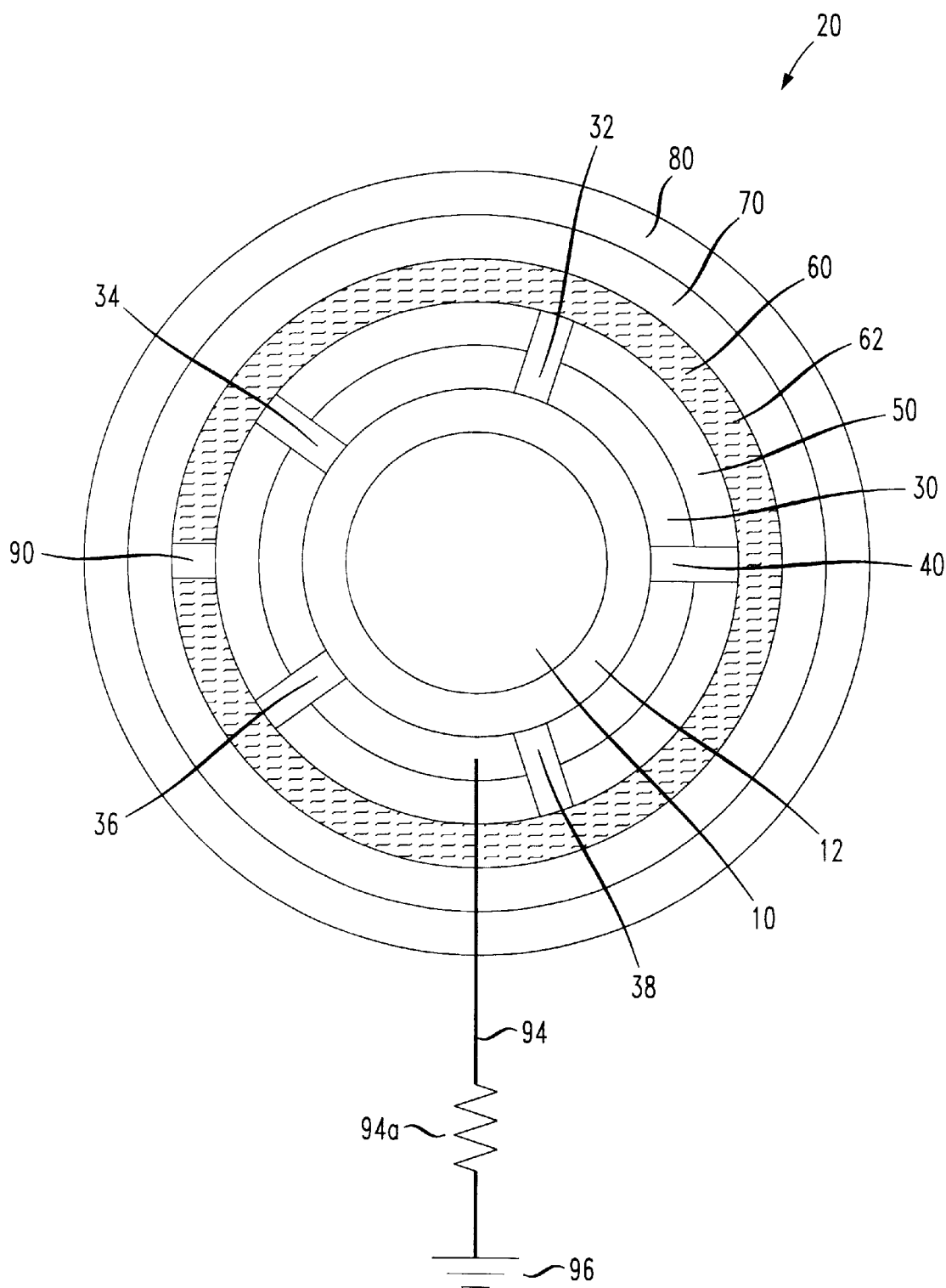
FIG. 1 shows a wrist band in accordance with a first embodiment of the present invention.

FIG. 1 shows wrist band 20 in accordance with an embodiment of the present invention. Wrist band 20 is shown surrounding skin 12 of a human wrist 10. Wrist band 20 includes conductive layer 30, reservoir retainer layer 50, reservoir layer 60, reservoir retainer layer 70, and fabric layer 80. In this embodiment the reservoir layer 60, along with retainer layers 50 and 70 function as a lotion storage device.

The conductive layer 30 and reservoir retainer layer 50 include holes 32, 34, 36, 38, and 40. In this embodiment, the holes 32, 34, 36, 38, and 40 along with the reservoir layers 50, 60, and 70 make up a lotion dispensing device. The holes 32, 34, 36, 38, and 40 allow lotion 62 from reservoir layer 60 to escape from the reservoir 60, through the reservoir retainer layer 50, the conductive layer 30 and to contact skin 12 of the wrist 10. The lotion 62 is preferably similar to the skin cream of lotions which exhibit some conductivity, such as electrostatic dissipative ("ESD") lotion, sold by Semtronics Inc. Reservoir layer 60 also includes a plug 90 which allows lotion to be inserted or removed from the reservoir 60. A grounding wire 94 is also shown in FIG. 1, connecting the conductive layer 30 to ground 96. The grounding wire 94 preferably includes one mega ohms (1 million ohms) worth of resistance 94a.

In this embodiment the reservoir retaining layers 50 and 70, the reservoir 60, and the holes 32, 34, 36, 38, and 40, together comprise a lotion dispensing device. The holes 32, 34, 36, 38, and 40 are preferably of a type that allow liquid to go out of the reservoir 60 but not to come back in which would be similar to a check valve in function, or may actually be small check valves.

In operation, a person places the wrist band 20 over the skin 12 of his or her wrist 10. Lotion 62 flows from the reservoir layer 60 through the holes 32, 34, 36, 38, and 40. The holes 32, 34, 36, 38, and 40 pass through the reservoir retainer layer 50 and through the conductive layer 30. The lotion 62 flows onto the skin 12 of the wrist 10. The lotion 62 flows at a slow consistent rate so that the skin 12 is consistently kept moist so that it can conduct.

A static discharge on a person, preferably flows through the skin 12 with the aid of lotion 62 and to the conductive layer 30. The conductive layer 30 in conjunction with the grounding wire 94 which includes grounding resistance 94a, and with ground 96, dissipates the static charge to prevent potential damage to electronic circuitry.

Figure 2:
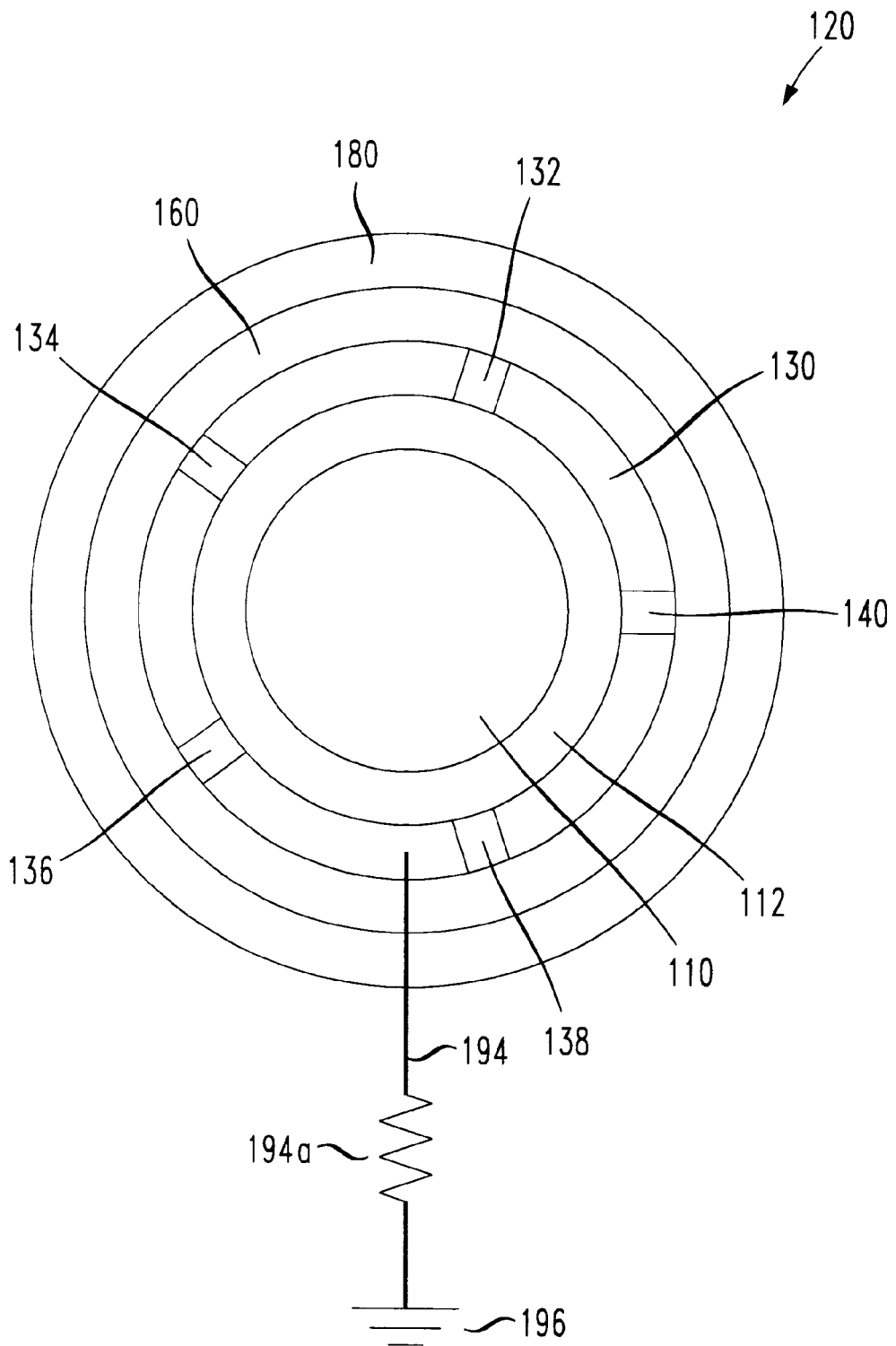
FIG. 2 shows a wrist band in accordance with a second embodiment of the present invention.

FIG. 2 shows a wrist band 120 in accordance with a second embodiment of the present invention. The wrist band 120 is comprised of conductive layer 130, permeable membrane layer 160, and fabric layer 180. The conductive layer 130 is comprised of holes 132, 134, 136, 138, and 140. The wrist band 120 surrounds wrist 110 which has skin 112. The conductive layer 130 is connected by grounding wire 194 having a resistance 194a to ground 196.

In operation the wrist band 120 functions as follows. An individual places the wrist band 120 around his or her wrist 110 and skin 112. Lotion is contained within the permeable membrane layer 160. The lotion seeps from the permeable membrane 160 through the holes 132, 134, 136, 138, and 140, through the conductive layer 130 and onto the skin 112. Preferably the size of the holes 132, 134, 136, 138, and 140 increases with heat so that more lotion is delivered to the skin 112 of a wrist 110. Preferably when it is cold, i.e. when the wrist band 120 is not being worn, the size of the holes 132, 134, 136, 138, and 140 shrink up so that less lotion is permeated from the permeable membrane 160. Microperforated "PE" or "PP" can be used for membrane layer 160 and stainless steel box can be used for the conductive layer 130. The holes 132, 134, 136, 138, and 140 preferably face the skin and range from 0.01 to 2 millimeters, and could have a permeable membrane or silastic material across the holes, to control the flow rate of lotion. More lotion is typically needed when it is hotter because when a person perspires he or she loses more fluids.

A static charge on a person or on his clothing, flows through the skin 112 on the wrist 110 aided by lotion dispensed from permeable membrane layer 160. The charge proceeds from skin 112 to conductive layer 130, then to grounding wire 194 having resistance 194a and finally to ground 196. The dissipation of the static charge again prevents damage to electronic circuitry.

Instead of a completely circular wrist band such as wrist bands 20 and 120, the present invention could be provided in any number of formats as appreciated by those skilled in the art, such as a watch band. The watch portion would be a container of lotion with holes and the conductive metal band would provide continuous contact with the skin.

The membrane layer 160 can be a thin polymer which has very small perforations or microperforations (the size of microns).

Figure 3:
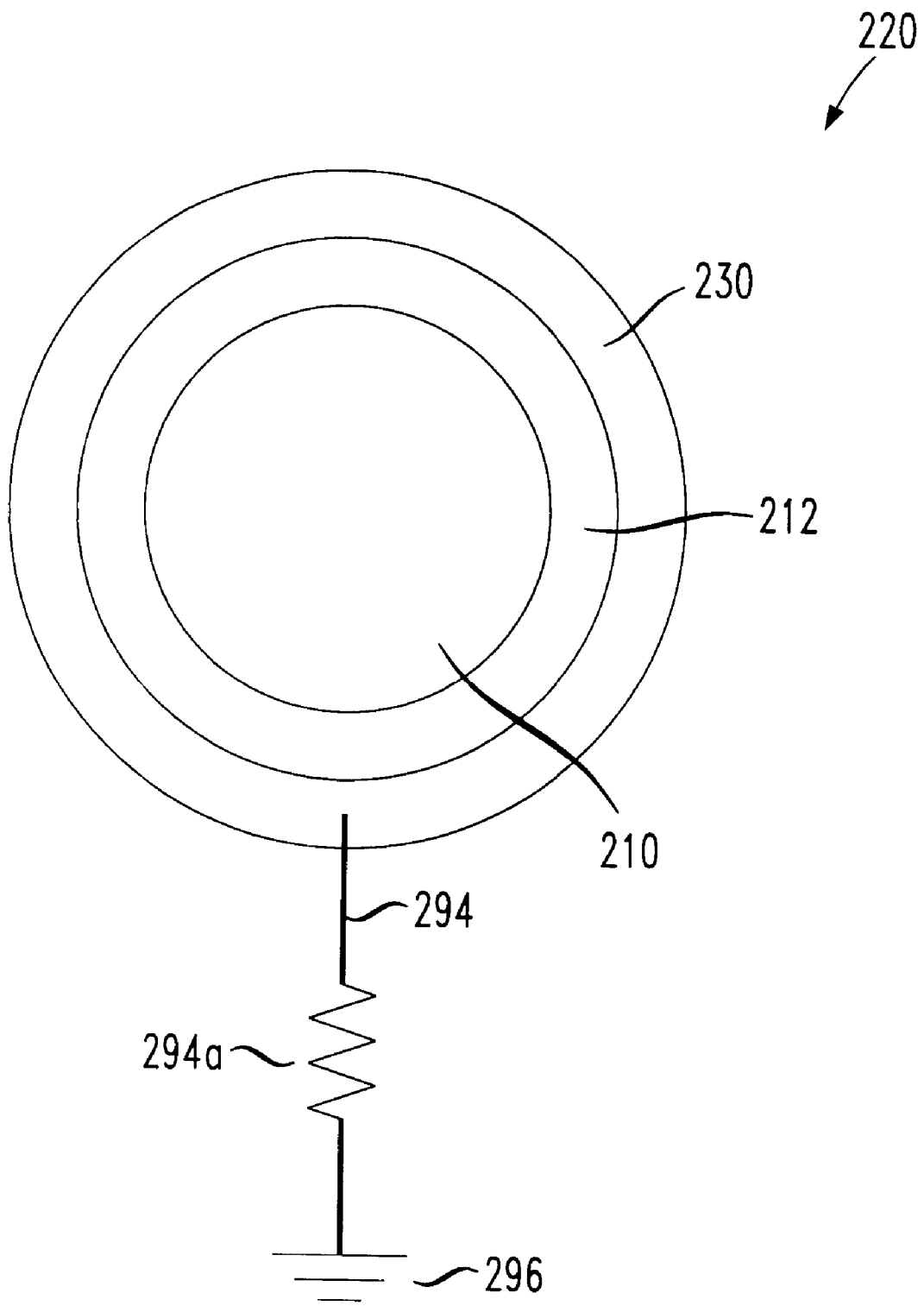
FIG. 3 shows a wrist band in accordance with a third embodiment of the present invention.

FIG. 3 shows a wrist band 220 in accordance with a third embodiment of the present invention. The wrist band 220 is comprised of a sponge layer 230. The sponge layer 230 comes in direct contact with skin 212 of a wrist 210. The sponge layer 230 is preferably also conductive. The sponge layer 230 is connected by grounding wire 294 having a resistance 294a to the ground terminal 296. The sponge layer 230 is preferably impregnated with lotion. The lotion is preferably a lotion which exhibits some conductivity, such as electrostatic dissipative ("ESD") lotion, sold by Semtronics Inc.

Preferably the layers such as conductive layer 30, elastic textile with conductive reservoir retainer layer 50, reservoir layer 60, reservoir retainer layer 70, and fabric layer 80 are elastic so that they can expand over a person's wrist and then contract to remain snugly fit on a person's wrist. The conductive reservoir layer 50 can be an elastic cotton with conductive threads. The fabric layer 80 can be elastic cotton or polyester.

Figure 4:
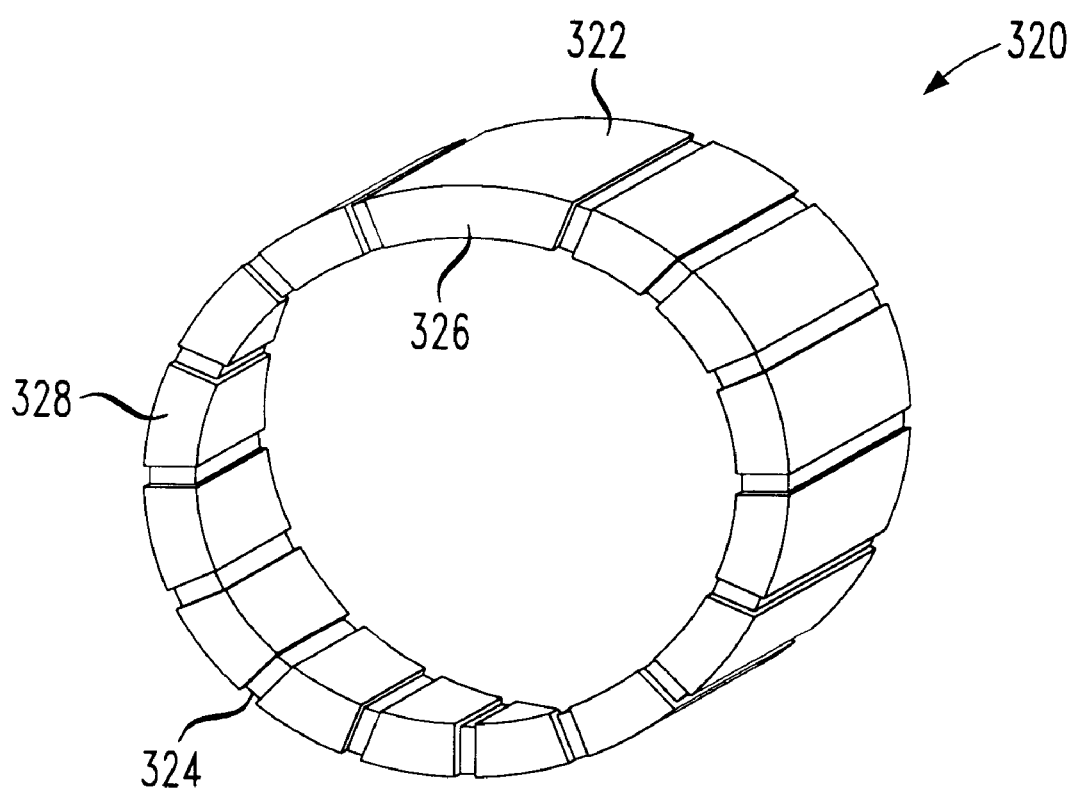
FIG. 4 shows a wrist band similar to a watch in accordance with another embodiment of the present invention.

FIG. 4 shows a wrist band 320 in accordance with another embodiment of the present invention. The wrist band 320 is comprised of a lotion filled reservoir 322, spring loaded flex segments 324, metal band element 328, and permeable membrane 326. An individual puts the wrist band 320 on his wrist like a watch. Lotion within the lotion filled reservoir 322 comes through the permeable membrane 326 and goes on the skin. The permeable membrane 326 may be comprised of holes such as holes 347, 348, and 349 in FIG. 5.

Figure 5:
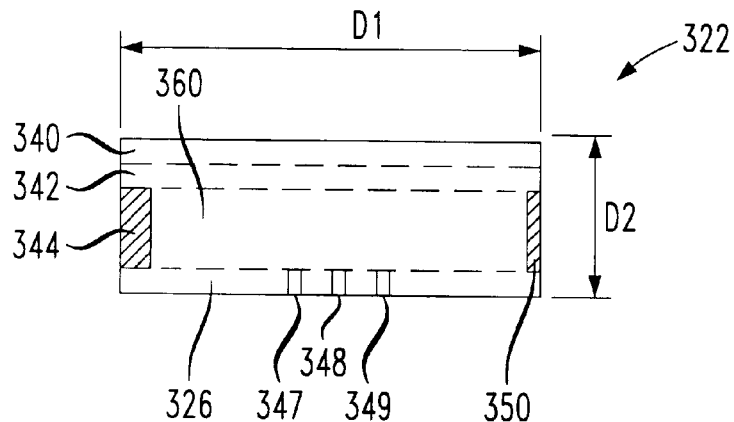
FIG. 5 shows a front cross sectional view of a lotion reservoir for use with the wrist band of FIG. 4.

FIG. 5 shows a front cross sectional view of a lotion reservoir 322 for use with the wrist band of FIG. 4. The lotion reservoir 322 includes top portion 340 and bottom portion 326 (the permeable membrane 326) which may be the same material as the metal band element 328. The bottom portion 326 includes holes 347, 348, and 349. The lotion reservoir 322 includes a plug 344 and a wall 350 which along with the top portion 340 and the bottom portion 326 enclose the inner reservoir 360. The inner reservoir 360 is preferably filled with lotion. The lotion reservoir 322 preferably has a height of D2 and a length of D1.

Figure 6:
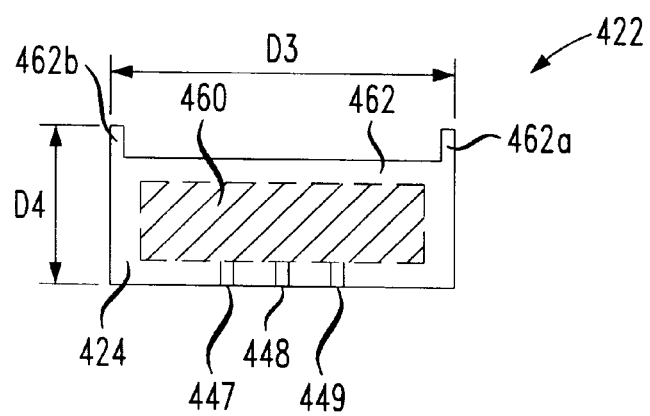
FIG. 6 shows a front cross sectional view of another type of lotion reservoir for use with the wrist band of FIG. 4.

FIG. 6 shows a front cross sectional view of another type of lotion reservoir 422 for use with the wrist band of FIG. 4. The lotion reservoir 422 includes permeable membrane 424 which includes holes 447, 448, and 449. The lotion reservoir 422 preferably has clip on edges 426a and 426b. A cover 462 surrounds the inner reservoir chamber 460 which contains a permeable membrane (such as a sponge).

We claim:

1. An apparatus comprising:
   a strap comprised of an outer layer which is shaped in the form of a closed loop and of a conductive inner layer;
   and a lotion dispensing device connected to the strap wherein the lotion dispensing device is within the outer layer of the strap.

2. The apparatus of claim 1 wherein:
   wherein the conductive inner layer includes a plurality of holes and the plurality of holes of the conductive inner layer are part of the lotion dispensing device.

3. The apparatus of claim 1 wherein:
   the lotion dispensing device is comprised of a lotion storage device.

4. The apparatus of claim 3 wherein:
   the lotion storage device is located on the periphery of the conductive inner layer.

5. The apparatus of claim 4 wherein:
   the lotion dispensing device is comprised of a reservoir filled with lotion.

6. The apparatus of claim 3 wherein:
   the lotion storage device is comprised of a reservoir filled with lotion.

7. The apparatus of claim 1 wherein:
   the lotion dispensing device is comprised of a permeable membrane.

8. The apparatus of claim 7 wherein lotion dispenses from the permeable membrane at a rate which is increased with heat.

9. The apparatus of claim 1 wherein the lotion dispensing device is comprised of a sponge.

10. The apparatus of claim 1 and further comprised of:
a grounding wire connected to the conductive inner layer.

11. The apparatus of claim 10 wherein the grounding wire is comprised of a resistance.

12. The apparatus of claim 11 wherein the resistance is about 1 mega-ohm.

13. The apparatus of claim 1 wherein the strap is in the form of a wrist band.

14. The apparatus of claim 13 wherein the strap is in the form of a watch band.

15. The apparatus of claim 1 wherein
the outer layer of the strap is comprised of a fabric material.

16. A method comprising the steps of:
applying a conductive strap around the circumference of a person's wrist; and
applying a lotion dispensing strap around the circumference of the conductive strap;
wherein the conductive strap has a plurality of holes for allowing the lotion dispensing strap to dispense lotion onto an individual's skin.

17. An apparatus comprising:
a conductive strap;
and a lotion dispensing device connected to the conductive strap;
and wherein the lotion dispensing device is comprised of a plurality of holes in the conductive strap and the size of each hole increases in response to a greater heat level.

18. An apparatus comprising:
a strap comprised of:
a reservoir outer retainer layer;
a reservoir inner retainer layer;
a reservoir;
a conductive layer;
a ground wire connected to the conductive layer;
wherein the strap is in the form of a wrist band.

19. The apparatus of claim 18 wherein:
the strap is further comprised of a fabric layer.

20. The apparatus of claim 19 wherein:
in the wrist band the layers are arranged from innermost to outermost in the following order:
the conductive layer is the innermost layer;
the reservoir inner retainer layer is next;
the reservoir is next;
the reservoir outer retainer layer is next;
and the fabric layer is the outermost layer.

* * * * *